United States Patent
Detamore et al.

(10) Patent No.: US 10,744,228 B2
(45) Date of Patent: Aug. 18, 2020

(54) METHACRYLATED DEVITALIZED CARTILAGE AND DEVITALIZED CARTILAGE PARTICLES

(71) Applicant: The University of Kansas, Lawrence, KS (US)

(72) Inventors: Michael Detamore, Lawrence, KS (US); Emily Beck, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 90 days.

(21) Appl. No.: 15/254,709

(22) Filed: Sep. 1, 2016

(65) Prior Publication Data

US 2017/0065742 A1 Mar. 9, 2017

Related U.S. Application Data

(60) Provisional application No. 62/214,109, filed on Sep. 3, 2015.

(51) Int. Cl.
*A61L 27/36* (2006.01)
*A61L 27/52* (2006.01)
(Continued)

(52) U.S. Cl.
CPC ....... *A61L 27/3612* (2013.01); *A61L 27/3687* (2013.01); *A61L 27/3691* (2013.01);
(Continued)

(58) Field of Classification Search
None
See application file for complete search history.

(56) References Cited

U.S. PATENT DOCUMENTS 4,656,137 A 4/1987 Balassa
8,017,155 B2 9/2011 Schwendeman et al.
(Continued)

FOREIGN PATENT DOCUMENTS

CN 101890184 B 7/2013
WO 1999022747 A1 5/1999
(Continued)

OTHER PUBLICATIONS

Visser et al., Tissue Eng. 00(00): 1-12 (2015).*
(Continued)

*Primary Examiner* — Erin M Bowers
(74) *Attorney, Agent, or Firm* — Maschoff Brennan; Jonathan M. Benns

(57) ABSTRACT

An implantable composition can include methacrylated solubilized devitalized cartilage (MeSDVC) with or without devitalized cartilage (DVC) particles. These compositions can be hydrogel precursors. After implantation, the MeSDVC may be crosslinked so as to form a hydrogel. The crosslinked hydrogel can include the DVC particles. A hydrogel precursor matrix (e.g., not crosslinked) can include a crosslinkable substance that can be crosslinked into a hydrogel, where DVC particles are included in the precursor matrix. The hydrogel precursor matrix can be located in a tissue defect site, such as a hole or recess in a cartilage or bone, and then crosslinked into a hydrogel that has the DVC particles therein.

20 Claims, 10 Drawing Sheets

(51) Int. Cl.
*A61L 27/54* (2006.01)
*A61L 27/48* (2006.01)

(52) U.S. Cl.
CPC .............. *A61L 27/48* (2013.01); *A61L 27/52* (2013.01); *A61L 27/54* (2013.01); *A61L 2400/06* (2013.01); *A61L 2430/06* (2013.01)

(56) References Cited

U.S. PATENT DOCUMENTS

| | | | |
|---|---|---|---|
| 8,221,500 | B2 | 7/2012 | Truncale et al. |
| 8,277,832 | B2 | 10/2012 | Detamore et al. |
| 2008/0077251 | A1 | 3/2008 | Chen et al. |
| 2008/0279825 | A1* | 11/2008 | Malinin .............. A61F 2/30756 424/93.7 |
| 2009/0024223 | A1 | 1/2009 | Chen et al. |
| 2009/0024224 | A1 | 1/2009 | Chen et al. |
| 2009/0024229 | A1 | 1/2009 | Chen et al. |
| 2011/0070271 | A1 | 3/2011 | Truncale et al. |
| 2011/0195107 | A1 | 8/2011 | Min et al. |
| 2011/0212894 | A1 | 9/2011 | Athanasiou et al. |
| 2013/0171197 | A1 | 7/2013 | Ho et al. |

FOREIGN PATENT DOCUMENTS

| | | |
|---|---|---|
| WO | 2009011849 A2 | 1/2009 |
| WO | 2012142569 A2 | 10/2012 |
| WO | 2014032748 A1 | 3/2014 |
| WO | 2015048317 A1 | 4/2015 |

OTHER PUBLICATIONS

Visser et al., Biomaterials. 37: 174-182 (2015).*
Levett et al., Acta Biomaterial. 10: 214-223 (2014).*
Boere et al., Acta Biomaterial. 10: 2602-2611 (2014).*
Kwon, JS et al., Injectable Extracellular Matrix Hydrogel Developed Using Porcine Articular Cartilage, International Journal of Pharmaceutics. Sep. 15, 2013. vol. 454. No. 1, pp. 183-191.
Garrigues, N. W., Little, D., Sanchez-Adams, J., Ruch, D. S., & Guilak, F. (Nov. 1, 2015). Electrospun Cartilage-Derived Matrix Scaffolds for Cartilage Tissue Engineering, Journal of Biomedical Materials Research Part A. Author Manuscript. J. Biomed Mater Res A. Nov. 2014; 102(11): 3998-4008. DOI:10.1002/jbm.a.35068.
Beck, Emily C. et al., Chondroinduction from Naturally Derived Cartilage Matrix: A Comparison Between Devitalized and Decellularized Cartilage Encapsulated in Hydrogel Pastes, Tissue Engineering: Part A. 2016. vol. 22. No. 7 and 8, pp. 665-679. DOI: 10.1089/ten.tea.2015.0546.
Beck, Emily C. et al., Chondroinductive Hydrogel Pastes Composed of Naturally Derived Devitalized Cartilage, Annals of Biomedical Engineering. Jan. 7, 2016. DOI: 10.1007/s10439-015-1547-5.
Visser, Jetze et al., Crosslinkable Hydrogels Derived from Cartilage, Meniscus, and Tendon Tissue, Tissue Engineering: Part A. 2015. vol. 00. No. 00, pp. 1-12. DOI: 10.1089/ten.tea.2014.0362.

* cited by examiner

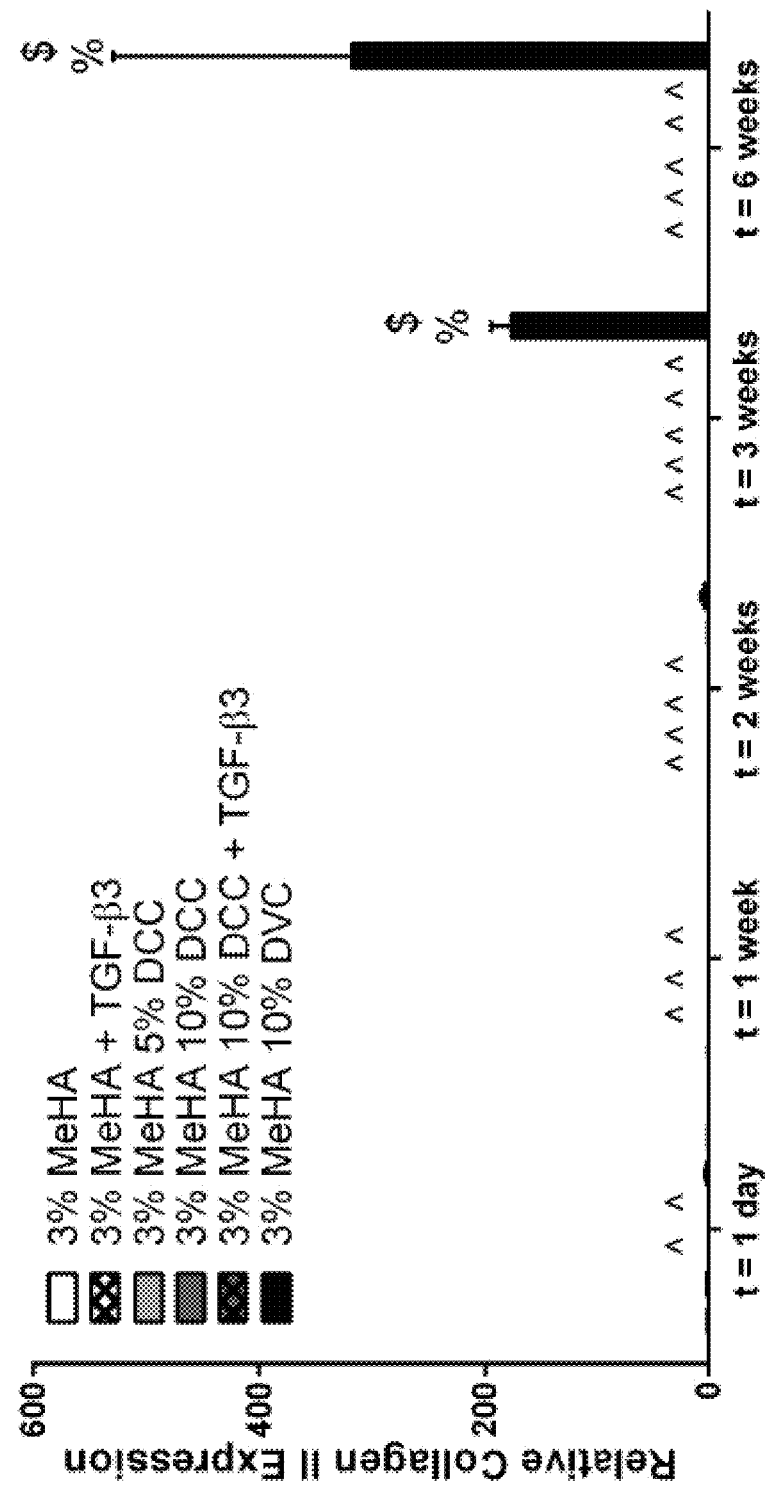

ized cartilage (DVC) particles. In one embodiment, a composition can include solubilized devitalized cartilage (SDVC). In one embodiment a composition can include methacrylated devitalized cartilage (MeDVC), which may be methacrylated solubilized devitalized cartilage (MeSDVC). In one embodiment, a composition can include methacrylated devitalized cartilage (MeDVC) containing devitalized cartilage (DVC) particles. In one embodiment, a composition can include methacrylated solubilized devitalized cartilage (MeSDVC) containing devitalized cartilage (DVC) particles. These compositions can be hydrogel precursors.

METHACRYLATED DEVITALIZED CARTILAGE AND DEVITALIZED CARTILAGE PARTICLES

CROSS-REFERENCE

This patent application claims priority to U.S. Provisional Ser. No. 62/214,109 filed Sep. 3, 2015, which provisional application is incorporated herein by specific reference in its entirety.

GOVERNMENT RIGHTS

This invention was made with government support under R01 DE022472 awarded by the National Institutes of Health (NIH). The government has certain rights in the invention.

BACKGROUND

Hydrogels have been used as tissue scaffolds for tissue regeneration. However, hydrogels are often designed to be implanted as a liquid or in a flowable format and then cured or crosslinked in situ. Such in situ curing or crosslinking often takes time to complete, which allows for the hydrogel components to leak away from the implant site before and during the curing or crosslinking process. As such, the in situ cured or crosslinked hydrogels shrink or otherwise do not fill an implant site. Also, it is unfavorable to have hydrogel components move away from the implant site, especially when loaded with a bioactive agent that needs to be located in the implant site for functionality.

Thus, it would be advantageous to have an improved system for forming hydrogels that have improved stability without leaking before or during curing or crosslinking.

SUMMARY

In one embodiment, a composition can include devitalized cartilage (DVC) particles. In one embodiment, a composition can include solubilized devitalized cartilage (SDVC). In one embodiment a composition can include methacrylated devitalized cartilage (MeDVC), which may be methacrylated solubilized devitalized cartilage (MeSDVC). In one embodiment, a composition can include methacrylated devitalized cartilage (MeDVC) containing devitalized cartilage (DVC) particles. In one embodiment, a composition can include methacrylated solubilized devitalized cartilage (MeSDVC) containing devitalized cartilage (DVC) particles. These compositions can be hydrogel precursors.

In one embodiment, a composition having the MeDVC, such as MeSDVC may be crosslinked so as to form a hydrogel. In one aspect, the crosslinked hydrogel can include the DVC particles.

In one embodiment, a hydrogel precursor matrix (e.g., not crosslinked) can include a crosslinkable substance that can be crosslinked into a hydrogel, where DVC particles are included in the precursor matrix. In one aspect, the hydrogel precursor matrix can be located in a tissue defect site, such as a hole or recess in a cartilage or bone. In one aspect, the hydrogel precursor can be implanted into a tissue defect and then crosslinked into a hydrogel that has the DVC particles therein. The hydrogel precursor matrix can include any crosslinkable composition that can be crosslinked into a hydrogel, such as methacrylated hyaluronic acid (MeHA) or any cartilage or extra cellular matrix.

In one aspect, a method of producing DVC can include freezing the cartilage (e.g., washed cartilage), and subsequently thawing the cartilage. The method can also include mixing the thawed cartilage with dry ice or otherwise refreezing or hardening the thawed cartilage, and then grinding the cartilage (e.g., course grinding to coarse or large particles). When dry ice is used, it can be evaporated off. Once the dry ice is evaporated, the course cartilage particles is considered to be devitalized cartilage (DVC) particles. The DVC particles can then be frozen and lyophilized. The DVC (lyophilized or un-lyophilized) can then be ground into fine particles, which may be performed by cryogrinding in a freezer mill. The finely ground DVC particles can then be frozen and lyophilized (e.g., second lyophilization). The DVC particles can then be filtered (e.g., using a size exclusion mesh) of a desired size cutoff.

In one embodiment, a method of making solubilized devitalized cartilage (SDVC) can include: obtaining cartilage; devitalizing the cartilage to obtain the DVC; mixing the DVC (e.g., powdered particles or non-powder) with acid to make an acidic DVC composition; adding pepsin to the acidic DVC composition to form a digested composition; stirring the digested composition; and adding a base to the digested composition to neutralize the pH to physiological pH so as to form the SDVC. The SDVC can be centrifuged to remove any un-solubilized DVC. The SDVC can be frozen and lyophilized.

In one embodiment, a method of making methacrylated solubilized devitalized cartilage (e.g., MeSDVC), can include; dissolving SDVC in water; adding an organic solvent (e.g., acetone) to make a water:solvent solution; adding glycidyl methacrylate, trimethylamine, and tetrabutyl ammonium bromide to the water:solvent solution; and stirring until obtaining methacrylated solubilized devitalized cartilage (MeSDVC) in the solution. The MeSDVC can then be obtained by removing the solution, such as by evaporation, lyophilization, precipitation (e.g., with acetone in excess), a combination thereof, or the like. In one aspect, the method can include precipitating the MeSDVC in excess acetone, dialyzing the precipitated MeSDVC for 2 days in DI water, and then lyophilizing dialyzed MeSDVC into a dry powder.

In one embodiment, a method of making a colloidal gel having a MeSDVC matrix and DVC particles can include mixing DVC particles into the MeSDVC.

In one embodiment, a method of making a hydrogel can include: obtaining a colloidal gel having a MeSDVC matrix with DVC particles therein; and crosslinking the MeSDVC. In one aspect, the crosslinking is performed via photo-activated crosslinking by shining a light have a proper wavelength for the crosslinking activator onto the composition.

In one embodiment, a method of inducing chondrogenesis can include: providing a composition described herein having DVC; implanting the composition into a body; and crosslinking the composition into a hydrogel for inducing chondrogenesis. In one aspect, the DVC includes particles. In one aspect, the composition includes MeSDVC. In one aspect, the MeSDVC includes bioactive agents therein, such as agents that induce chondrogenesis.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 5A includes a graph showing the comparative relative collagen II expression for different hydrogel precursor compositions with DCC versus DVC.

DETAILED DESCRIPTION

Figure 1A:
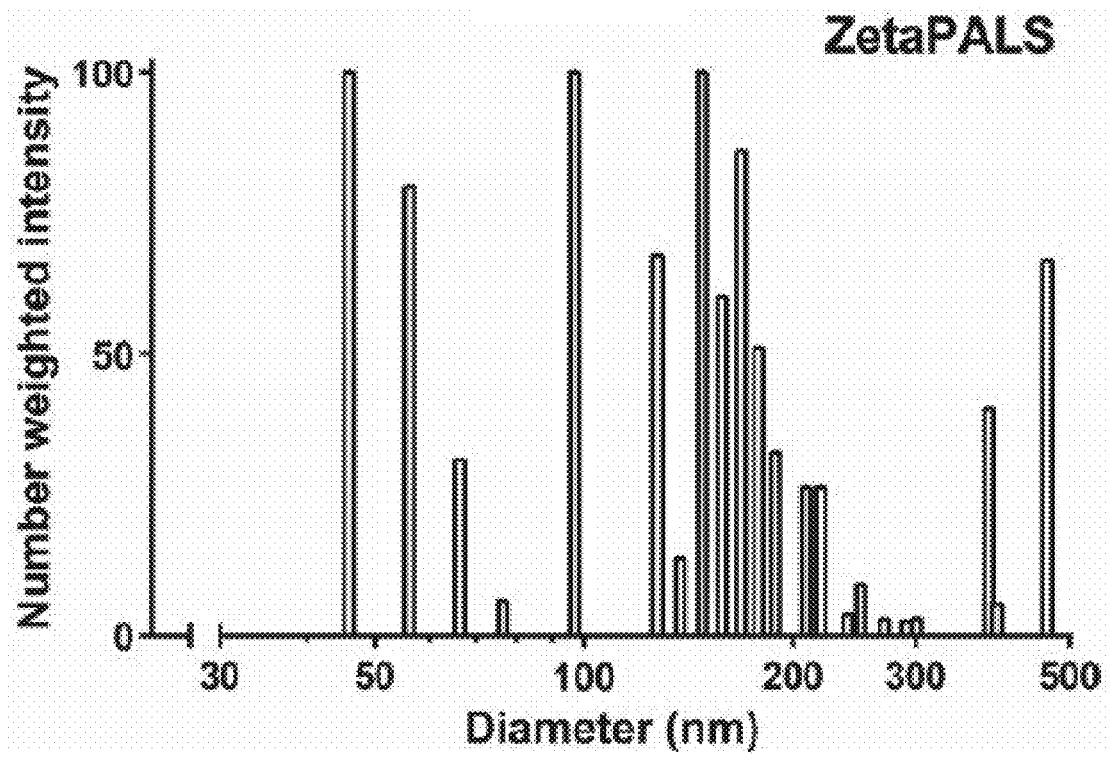
FIG. 1A includes a graph showing the DVC particle size distribution by number weighted intensity.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology relates to hydrogel precursors, hydrogels and components thereof, where the hydrogels can be used as tissue scaffolds for tissue regeneration and engineering. The hydrogels can be prepared from hydrogel precursors, that when processed, result in a stable hydrogel. The stable hydrogel can have stability for some duration of time, and may also be biodegradable to break down over time. The hydrogel and hydrogel precursors can include processed cartilage as a matrix and processed cartilage particles for structural support and enhanced chondrogenic activity. The hydrogel components may include a colloidal gel paste that exhibits a yield stress prior to curing or crosslinking, which allows for the colloidal gel paste to be implanted into an implant site (e.g., defect site) so as to be substantially or fully retained therein before, during, and after curing or crosslinking.

In one embodiment, devitalized cartilage (DVC) can be used as a tissue scaffold material in the hydrogel and hydrogel precursor compositions. DVC may include components that can be used as building blocks of cartilage, such as glycosaminoglycans (GAGs) and collagen, and may include bioactive proteins to promote attachment, growth, and differentiation of cells on a tissue scaffold material. The DVC can be formed into nanoparticles for inclusion in a colloidal gel that is cured or crosslinked into a hydrogel, and which may facilitate cellular attachments and influence chondrogenic gene expression. Accordingly, DVC matrix or particulates (e.g., nanoparticles) can be used as a hydrogel component in colloidal gels described herein, as well as the hydrogels formed therefrom.

In one embodiment, the DVC may be methacrylated to be methacrylated DVC (MeDVC) for use in matrix or particulate form. Methacrylation of DVC can be performed similarly to the methacrylation of Decellularized Cartilage (DCC) or HA, such as described herein. In one aspect, the DVC can be solubilized into solubilized DVC (SDVC) before being methacrylated into methacrylated solubilized DVC (MeSDVC). The MeDVC or MeSDVC matrix can be combined with DVC particles to form a colloidal gel for use as a tissue scaffold. Also, MeDVC or MeSDVC matrix may be combined with DVC particles to form a colloidal gel for use as a tissue scaffold. Additionally, DVC or SDVC matrix may be combined with MeDVC particles for use as a tissue scaffold. In one aspect, the combination of MeDVC or MeSDVC matrix with DVC particles can be beneficial by having suitable rheology and yield stress so as to be useful for tissue scaffolds, such as by implanting a colloidal gel thereof into an implant site (e.g., cartilage defect) with in situ curing or crosslinking.

In one embodiment, the colloidal gel (e.g., colloidal gel paste) composition described herein can be applied to an implant site for cartilage regeneration. The colloidal gel may also include cells (e.g., living cells) for delivery into the implant site, and thereby the colloidal gel can be used as a delivery vehicle for cells to the implant site, such as a cartilage defect for cartilage regeneration. The colloidal gel may also include bioactive agents, whether nucleic acid, nucleic acid complexes, polypeptides, proteins, small molecules, or traditional drugs as well as other substances, and thereby the colloidal gel can be used as a delivery vehicle for bioactive agents to the implant site. Examples of bioactive agents may include growth factors, such as cartilage and bone growth factors, or other tissue growth factors. Thus, the colloidal gels can be implanted into a defect site in any type of tissue (e.g., cartilage, bone, etc.) and then cured or crosslinked to facilitate regeneration of the tissue.

The colloidal gel composition allows a surgeon or other medical professional to place the material into a defect site without the colloidal gel or components thereof leaking from the defect site. Once placed, the medical professional can cure or crosslink the colloidal gel into a hydrogel, which includes the particulates therein. For a photoactivated crosslinking, the medical professional can shine a light on the implanted colloidal gel for curing or crosslinking. In order to facilitate such implantation and in situ curing or crosslinking, the colloidal gel composition can be created to include sufficient DVC particles in order to have rheological properties of a paste-like material that can be placed into a defect site and remain in place, and without contracting or shrinking in size before, during, or after curing or crosslinking.

It was surprisingly and unexpectedly found that the DVC particles had improved bioactivity and chondroinductivity relative to other particles in a colloidal gel. Particularly, the data shows that the DVC had improved bioactivity and chondroinductivity compared to DCC particles.

In one embodiment, devitalized cartilage extracellular matrix (DVC) can be mixed with DVC that had been solubilized and methacrylated (MeSDVC) to create hydrogels that are chondroinductive. Hydrogel precursor compositions of 10% MeSDVC or 10% MeSDVC with 10% DVC can have non-Newtonian behavior. Cells (e.g., rat bone marrow stem cells (rBMSCs) or others, such as human stem cells) can be mixed in the precursor compositions, and then implanted and crosslinked.

The method of preparing the hydrogel can result in a covalently crosslinked hydrogel with the matrix and particles being cartilage extracellular matrix (ECM). The hydrogel can include cartilage matrix particles, and as a consequence, the hydrogel precursor has a yield stress before crosslinking, which allows implantation of the hydrogel precursor (e.g., colloidal gel) without leaking from the implantation site. The colloidal gels are prepared to be dynamic paste-like materials prior to crosslinking that can be molded into place and cured/crosslinked after placement. These colloidal gels are cohesive through disruptable particle interactions, and can be used to treat tissue defects by delivering bioactive signals and promoting new tissue formation.

In one embodiment, non-particulate gels of MeSDVC can have a yield stress. For example, 10% MeSDVC alone had a yield stress of over 700 Pa. A composition of 10% DVC particles had a yield stress of only 58 Pa. However, when 10% MeSDVC is combined with 10% DVC particles the colloidal gel can have a yield stress of over 1800 Pa, which is synergistic and surprising and unexpected. Additionally, when cells were mixed in with the 10% MeSDVC and 10% DVC particle material, the cells did not significantly affect the yield stress value, which is advantageous because these materials can be mixed with cells and still allow for appropriate shaping and contouring to avoid leakage prior to crosslinking. Although the 10% MeSDVC and 10% DVC precursor solutions are easily molded, shaped, and extruded through a syringe, there may be applications where the yield stress may need to be increased or reduced. In this case, the concentrations of MeSDVC and DVC can be altered, either being independently increased or decreased to obtain the desired yield stress.

It has been found that the use of DVC (e.g., MeSDVC and DVC particles) can increase production of cartilage. For MeSDVC alone, there was an upregulation of Sox-9. Also, aggrecan was upregulated at two weeks when rBMSCs were exposed to DVC particles, with or without TGF-133 supplementation. Furthermore, at 6 weeks, the DVC particle groups with and without TGF-133 had a relative collagen II expression that was 40 and 78 fold higher, respectively, than that of MeSDVC alone. Additionally, collagen II expression of the DVC particle groups significantly increased over the culture period, whereas the relative collagen II expression of the MeSDVC only group did not change. Also, a slight increase in collagen II staining was observed in the DVC particle groups, in agreement with the gene expression data. A slight increase in aggrecan staining was noted in the 10% MeSDVC group, and this group was noted to have a significantly higher aggrecan gene expression than the other groups at day 1. Although the TGF-133 group had no discernable changes in aggrecan staining over the 6 weeks, it had the highest aggrecan gene expression at 2 weeks. Even though at weeks 1 and 2, the relative collagen I expression in the DVC particle groups was higher, at day 1 the relative collagen I expression in the DVC particle groups was significantly lower. Furthermore, collagen I staining actually increased slightly in the MeSDVC group over the culture period, while it decreased in the DVC particle groups. Overall, the gene expression and histological data pointed toward the DVC particles as a component for upregulating chondrogenic genes.

Accordingly, the DVC particles can facilitate chondrogenesis, and facilitate reducing hydrogel contraction in order for the shaped colloid gel and resulting hydrogel to remain shape stable without shrinkage. As such, including the DVC particles in a MeDVC hydrogel can inhibit contraction and disintegration that could potentially hinder successful cartilage regeneration. The data shows that the inclusion of DVC particles affected gel contraction and swelling, where gels composed only of MeSDVC contracted by 18% over the culture period, but the gels containing DVC particles did not have a significant change in volume.

The compressive moduli was found to be in the range from 70-170 kPa for all of the 10% MeSDVC and 10% MeSDVC+10% DVC groups. Also, a compressive modulus of approximately 675 kPa was obtained in the acellular 20% MeSDVC group, which is on the same order of magnitude as native articular cartilage. Also, both of the 10% MeSDVC groups (e.g., with or without 10% DVC particles) had a significant reduction in their mechanical properties over the course of the 6 weeks. However, it is possible that once these materials are implanted in vivo, the biomechanical stimulation may help increase matrix synthesis and improve the mechanical properties.

Even though DVC particles may hinder the biomechanical performance and are not necessarily needed to induce a yield stress if using MeSDVC as a hydrogel precursor and hydrogel material, the particles can contribute to enhanced chondrogenesis and the elimination of hydrogel contraction. Because the DVC particles contain mostly unaltered cartilage ECM, other than the DVC particles are cryoground, they may retain more of the bioactivity of the cartilage matrix than MeSDVC since MeSDVC is altered cartilage ECM, where it contained 97% less DNA and 41% fewer GAGs than DVC. Proteoglycans, specifically aggrecan in cartilage matrix, are found extensively in native cartilage matrix and are thought to be a reservoir of several growth factors. As such, some of the growth factors inducing chondrogenesis within cartilage ECM may have been altered or removed in the processing of MeSDVC, but are retained in DVC. Thus, DVC particles can provide an improvement to MeSDVC hydrogels.

In one embodiment, the processing of MeSDVC can be used to remove DNA therefrom. For example, the low pH exposure during the solubilization process can denature the DNA to a single-stranded state that can hydrolyze and further degrade the DNA. Furthermore, the dialysis step after methacrylation can remove these degraded DNA segments and low molecular weight nucleotides and amino acids, leaving behind higher molecular weight methacrylated GAGs and collagen.

SEM imaging revealed that the DVC particles were approximately 110 μm in diameter or smaller and were noted to be heterogeneous in size and morphology. Methacrylation of SDVC into MeSDVC was confirmed via $^1$H NMR by the emergence of methacrylate peaks between 5 and 6.5 ppm. The DNA content of the DVC particles was 1170±68 ng DNA per mg dry DVC, where the SDVC and MeSDVC had DNA contents that were 92% and 97% less than DVC, respectively. The GAG content of the DVC particles was 380±57 μg GAG per mg dry DVC, and the SDVC and MeSDVC had GAG contents that were 44% and 41% less than that of DVC, respectively. The hydroxyproline content of DVC was 48.60±0.58 µg hydroxyproline per mg dry DVC, where the hydroxyproline content of SDVC was 26% lower than that of DVC. The hydroxyproline content of MeSDVC was not significantly different from that of DVC, but was 41% higher than that of SDVC.

Figure 1B:
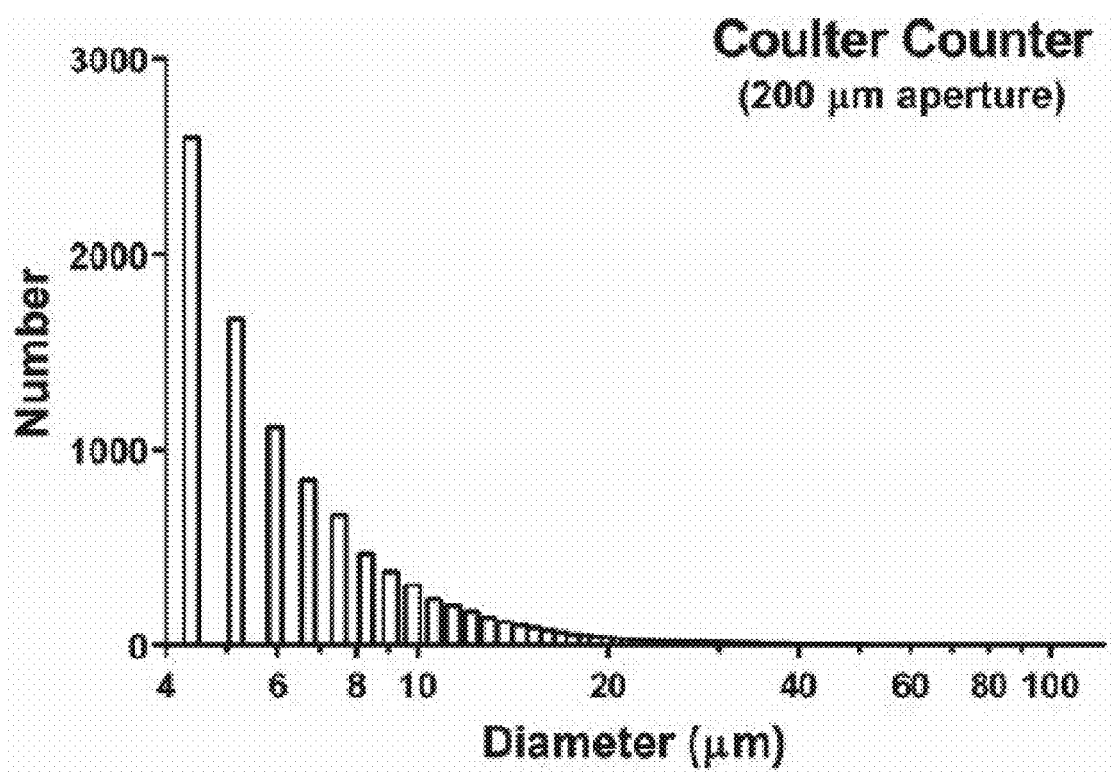
FIG. 1B includes a graph showing the particle size distribution where a fast majority are below 20 microns.

Particle sizing further demonstrated the heterogeneity of the DVC particles beyond aforementioned SEM imaging, showing a large size distribution in both the micro- and nano-ranges, with a significant number of particles with diameters below 200 nm (FIG. 1A), and the vast majority below 20 µm in diameter (FIG. 1B).

The DVC particles can be obtained by obtaining cartilage; mixing the cartilage with dry ice; grinding the mixture of dry ice and cartilage to obtain ground cartilage; and removing the dry ice from the ground cartilage. The process may also include cryogrinding the ground cartilage with a freezer mill; filtering the cryoground cartilage with a sieve to remove large particulates, and lyophilizing the ground cartilage to obtain a dry powder. Size exclusion filtering, such as with a filter or sieve having apertures with the desired size, can be used to select particle sizes, and series of such filtering can be used to separate different particles sizes from each other. For example, the first filter can allow any particles less than 300 microns through, then the next filter can block particles larger than 200 microns (e.g., to collect particles 200-300 microns), then the next filter can block particles larger than 100 microns (e.g., to collect particles 100-200 microns), then the next filter can block particles larger than 50 microns (e.g., to collect particles 50-100 microns), then the next filter can block particles larger than 25 microns (e.g., to collect particles 25-50 microns), then the next filter can block particles larger than 10 microns (e.g., to collect particles 10-25 microns), then the next filter can block particles larger than 5 microns (e.g., to collect particles 5-10 microns), and then the next filter can block particles larger than 1 micron (e.g., to collect particles 1-5 microns). However, any of these ranges may be collected or omitted from the DVC particles used in the formation of the hydrogel precursors and hydrogels. Examples of specific sieve sizes used for filtering can be 45 microns and 105 microns, so as to collect particles larger, smaller, and therebetween.

The size exclusion filtering may also be done in the nanometer range, such as the first filter can allow any particles less than 300 nm through, then the next filter can block particles larger than 200 nm (e.g., to collect particles 200-300 nm), then the next filter can block particles larger than 100 nm (e.g., to collect particles 100-200 nm), then the next filter can block particles larger than 50 nm (e.g., to collect particles 50-100 nm), and then the next filter can block particles larger than 25 nm (e.g., to collect particles 25-50 nm).

Macroscopic observation of hydrogel precursors revealed non-Newtonian and paste-like behavior in all precursors. Furthermore, all solutions except the 5% DVC (e.g., no MeSDVC) and 10% DVC (e.g., no MeSDVC) groups were able to be shaped and molded into a sphere, where it was noted that the pastes incorporating DVC particles into a matrix were easier to shape and manipulate compared to only MeSDVC matrix. Shape retention after extrusion through a 3 mL syringe was indicated by the fluids that retained the diameter of the syringe orifice. All pastes exhibited shape retention except the 5% DVC group, which spread out over 2 times the diameter of the syringe orifice. Furthermore, all formulations containing MeSDVC were able to be crosslinked to maintain extrusion shape.

Figure 2A:
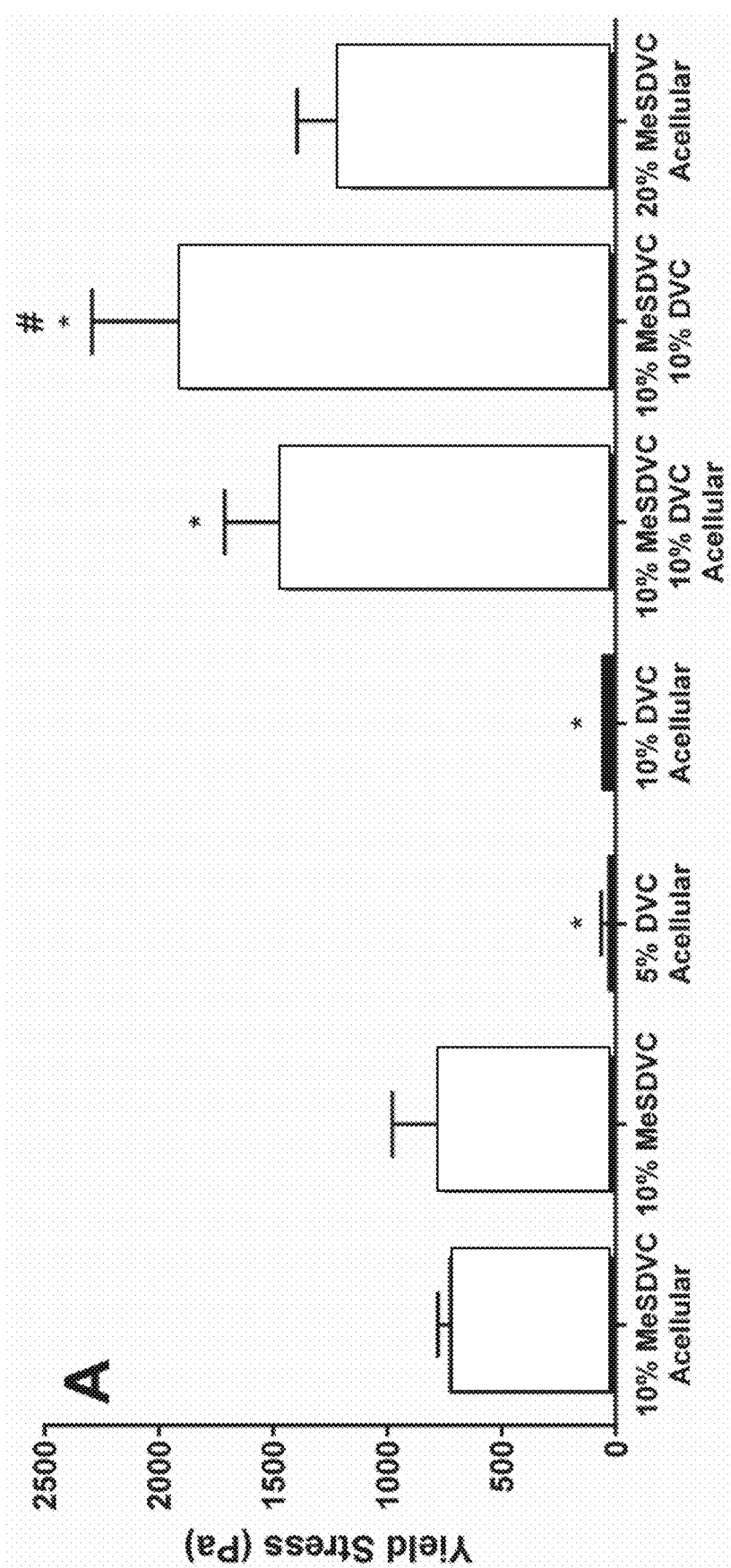
FIG. 2A includes a graph showing the comparative yield stresses for different hydrogel precursor compositions.

Additionally, all solutions exhibited a yield stress (FIG. 2A). The yield stress of 10% MeSDVC acellular group was 725±55 Pa, where the difference in yield stress compared to its respective cellular group was not significant. The 5% DVC only and 10% DVC only groups had yield stresses that were 96% and 92% lower, respectively, than that of 10% MeSDVC, while the MeSDVC+DVC acellular group had a yield stress that was 94% higher than that of 10% MeSDVC (FIG. 2A). Furthermore, when cells were mixed into the MeSDVC+DVC group, the yield stress was not significantly different from the acellular group, but it was 62% higher than that of the 20% MeSDVC acellular group.

In view of the data, it is expected that the yield stress can be modulated to desired levels for particular uses by modulating the amount of MeSDVC and/or DVC particles as well as adding rheology modifying substances (e.g., polysaccharides or synthetic polymers). As such, the values reported herein for yield stress may be modulated to increase or decrease by 1%, 2%, 5%, 10%, 25%, 50%, or 75%. For example, for MeDVC the yield stress may be 600-700 Pa, or higher than 5000 Pa, or even in a range of 200-1000 Pa. For MeDVC+DVC particles can have a yield stress from 1000-2000, where about 1500 Pa and about 1750 Pa are shown.

Figure 2B:
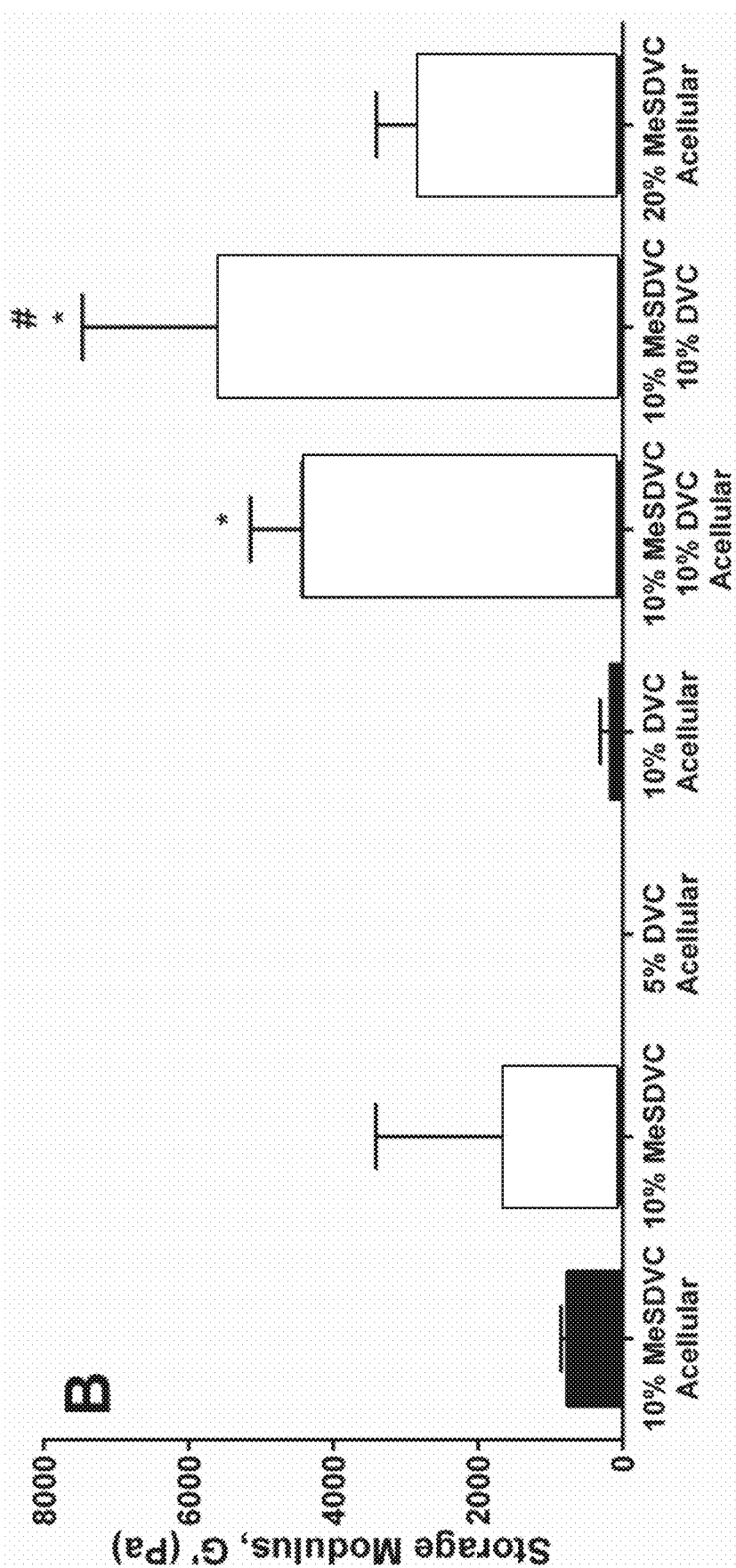
FIG. 2B includes a graph showing the comparative storage modulus for different hydrogel precursor compositions.

All solutions exhibited viscoelastic behavior, which was indicated by a measurable storage modulus, although the storage modulus of the 5% DVC was the lowest at 1.33±0.80 Pa (FIG. 2B). The storage modulus of the 10% MeSDVC acellular group was 773±84 Pa. The only groups that were significantly different from the 10% MeSDVC acellular group were the acellular and cellular MeSDVC+DVC groups, where their storage moduli were 5.7 and 7.2 times higher than that of the 10% MeSDVC acellular group, respectively. The storage modulus of the MeSDVC+DVC cellular group was 2 times higher than that of the 20% MeSDVC acellular group. Accordingly, the inclusion of DVC particles shows an increase in storage modulus.

In view of the data, it is expected that the storage modulus can be modulated to desired levels for particular uses by modulating the amount of MeSDVC and/or DVC particles as well as adding modifying substances. As such, the values reported herein for storage modulus may be modulated to increase or decrease by 1%, 2%, 5%, 10%, 25%, 50%, or 75%.

One day after crosslinking, the compressive modulus of the 10% MeSDVC acellular group was 135±37 kPa. None of the groups were significantly different from the 10% MeSDVC acellular group except the 20% MeSDVC acellular group, which had a modulus of 675±130 kPa. Six weeks after crosslinking, the compressive modulus of the 10% MeSDVC acellular group was 32±12 kPa, although there were no significant differences compared to other groups. However, over the 6 weeks of culture, while most of the groups did not deviate significantly from their original compressive modulus, the compressive modulus of the 10% MeSDVC acellular and cellular groups reduced by 77% and 86%, respectively.

The only group that had a significantly lower swelling degree than that of the 10% MeSDVC group, which had a swelling degree of 10.5±3.5 after swelling to equilibrium, was the 20% MeSDVC acellular group, where its swelling degree was 36% lower than that of the 10% MeSDVC group.

Figure 3:
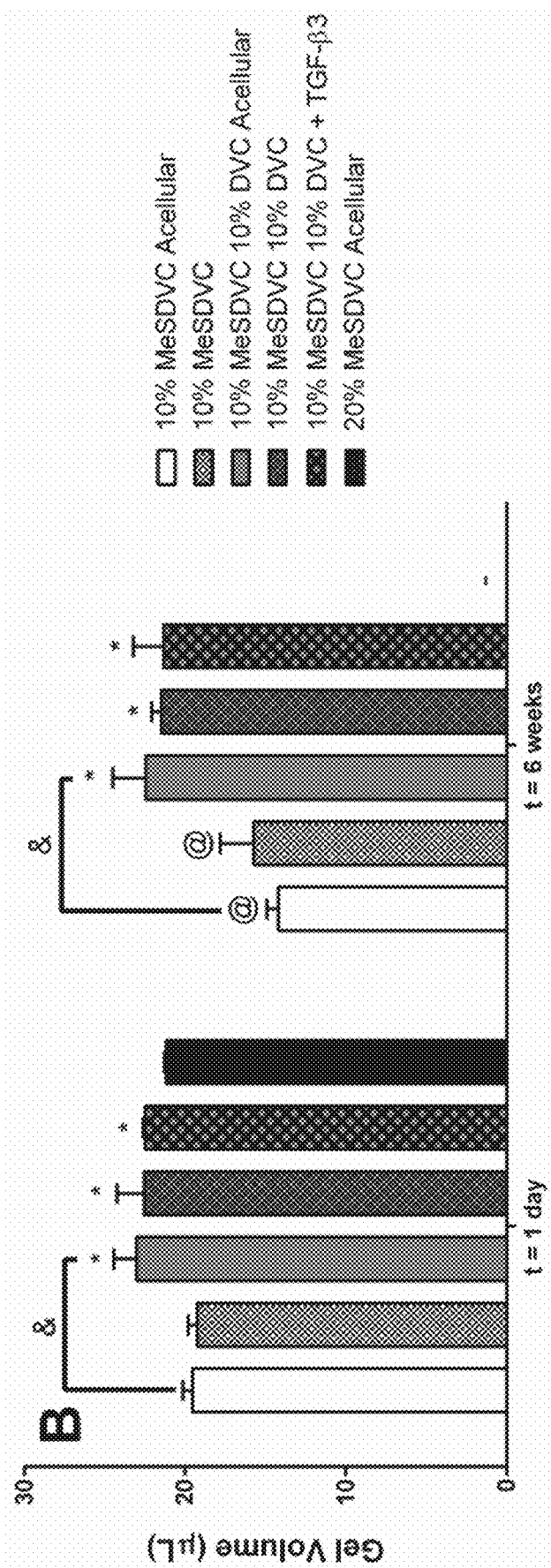
FIG. 3 includes a graph showing the comparative gel volume for different hydrogel precursor compositions at one day and 6 weeks after crosslinking.

At one day after crosslinking and swelling to equilibrium, the gel volume of the 10% MeSDVC group was 19.26±0.54 µL, where the volumes of the MeSDVC+DVC cellular, acellular, and TGF-β3 exposed groups were 17%, 20%, and 17% higher, respectively (FIG. 3). Furthermore, the volume of the MeSDVC+DVC group was 22.6±1.7 μL and it was not significant from its respective acellular and growth factor exposed group. At 6 weeks after crosslinking, again all three of the MeSDVC+DVC groups had significantly higher volumes than that of the 10% MeSDVC group (FIG. 3). The volume of the 10% MeSDVC group was 15.8±2.1 μL, while the volume of the cellular MeSDVC+DVC group was 36% larger. Over the course of 6 weeks, the only groups that had a significant change in volume were the 10% MeSDVC acellular and cellular groups, where they each decreased in volume by 27% and 18%, respectively (FIG. 3). The volumes of all three MeSDVC+DVC groups remained constant throughout the 6 week study. This shows that the MeSDVC+DVC has very little contraction, so when implanted it will stay at the implant site (e.g., stay in defect). Accordingly, the DVC particles provide a benefit to inhibit shrinkage and allow for use as an implant.

At 6 weeks, there were no discernable changes in any of the constructs other than the DVC-containing groups appeared to have a decreased cell density compared to their respective cell densities at day 1. However, throughout culture, the cells remained evenly distributed. Saf-O stained MeSDVC and DVC particles a dark red/orange color and the staining intensity of the DVC particles appeared to fade over the 6 weeks in culture. All groups stained for collagen II, where the collagen II staining for the DVC-incorporated groups was slightly darker at 6 weeks compared to at 1 week. The 10% MeSDVC group had a slight increase in collagen I staining over the culture period, whereas the DVC-incorporating groups had a slight decrease in collagen I staining. The MeSDVC+DVC group had the least amount of collagen I staining at 6 weeks. Aggrecan staining revealed a slight increase in aggrecan deposition in the 10% MeSDVC gels over the 6 week culture period. Additionally, the MeSDVC+DVC group had an increase in aggrecan staining over the course of the 6 weeks. Finally, no discernable changes in aggrecan staining was observed at 6 weeks for the MeSDVC+DVC+TGF-β3 group compared to its aggrecan staining at day 1.

It was also found that DVC, lacking the additional chemical processing steps in DCC to remove cell content, provides a more chondroinductive hydrogel. Also, the DVC can provide improved yield stress and storage modulus compared to DCC in MeHA hydrogels, which can also be improved when in MeSDVC hydrogels. It was surprisingly and unexpectedly found that the compositions with DVC particles were superior to compositions with DCC particles in shape retention and chondroinductivity and rheological performance.

SEM imaging revealed that DVC and DCC microparticles were approximately 45 μm in diameter or smaller and were noted to be heterogeneous in size and morphology. The DCC microparticles were observed to have smoother surfaces overall in comparison to the DVC microparticles, and thereby the rougher DVC particles may have improvements in rheology due to the rougher surfaces.

Macroscopic observation of hydrogel precursor formulations revealed non-Newtonian and paste-like behavior in hydrogel precursors containing at least 5% DCC. Shape retention after extrusion through a 3 mL syringe, which was indicated by the fluid retaining the diameter of the syringe orifice after extrusion and after crosslinking, was noted in the 10% DCC and MeHA+DVC acellular groups. The remaining solutions spread out to 2-3 times the diameter of the syringe orifice.

Figure 4A:
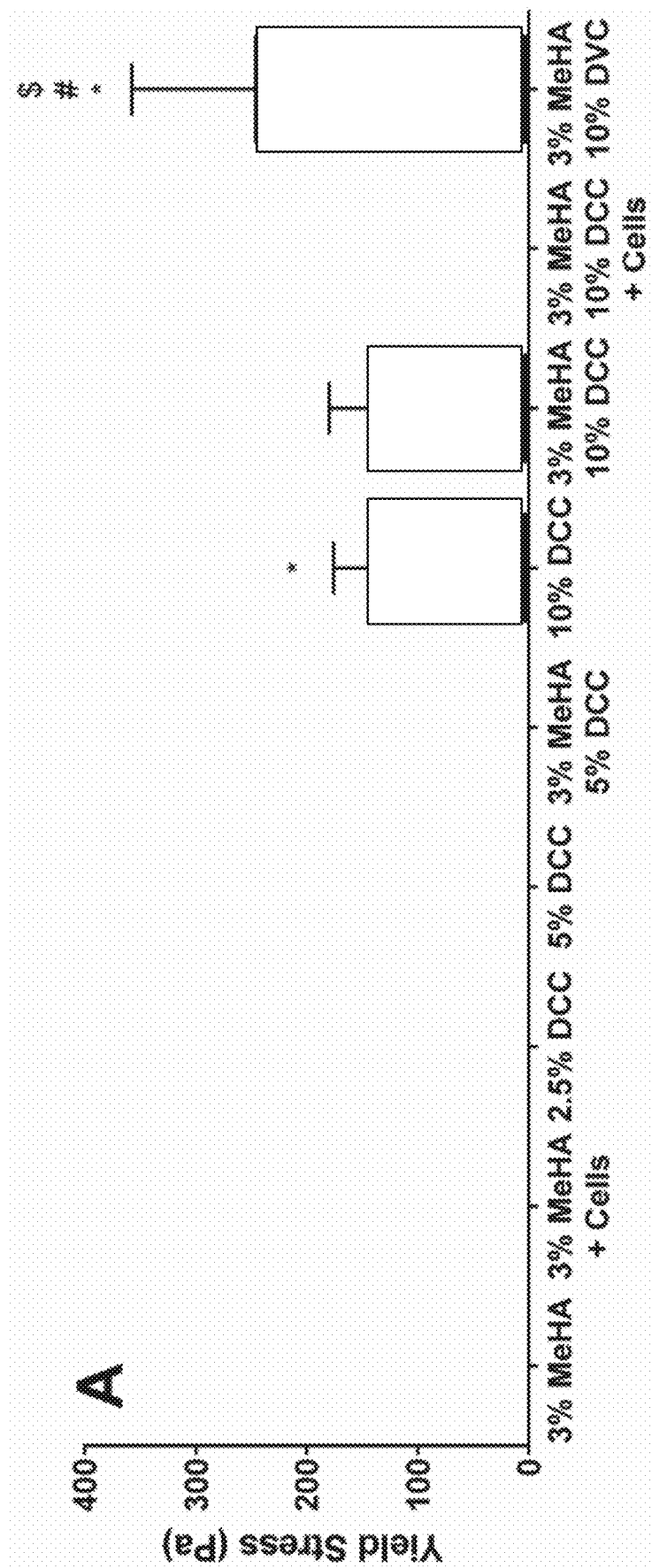
FIG. 4A includes a graph showing the comparative yield stresses for different hydrogel precursor compositions with DCC versus DVC.

Solutions exhibiting a measurable yield stress were the 10% DCC, MeHA+10% DCC, and MeHA+DVC formulations (FIG. 4A). The 10% DCC had a yield stress of 143±33 Pa, while adding MeHA to 10% DCC reduced the yield stress to 92±88 Pa, although the reduction was not significant. The yield stress of the MeHA+DVC group was 2.7 and 1.7 times greater than that of the MeHA+10% DCC and 10% DCC groups, respectively (FIG. 4A).

Figure 4B:
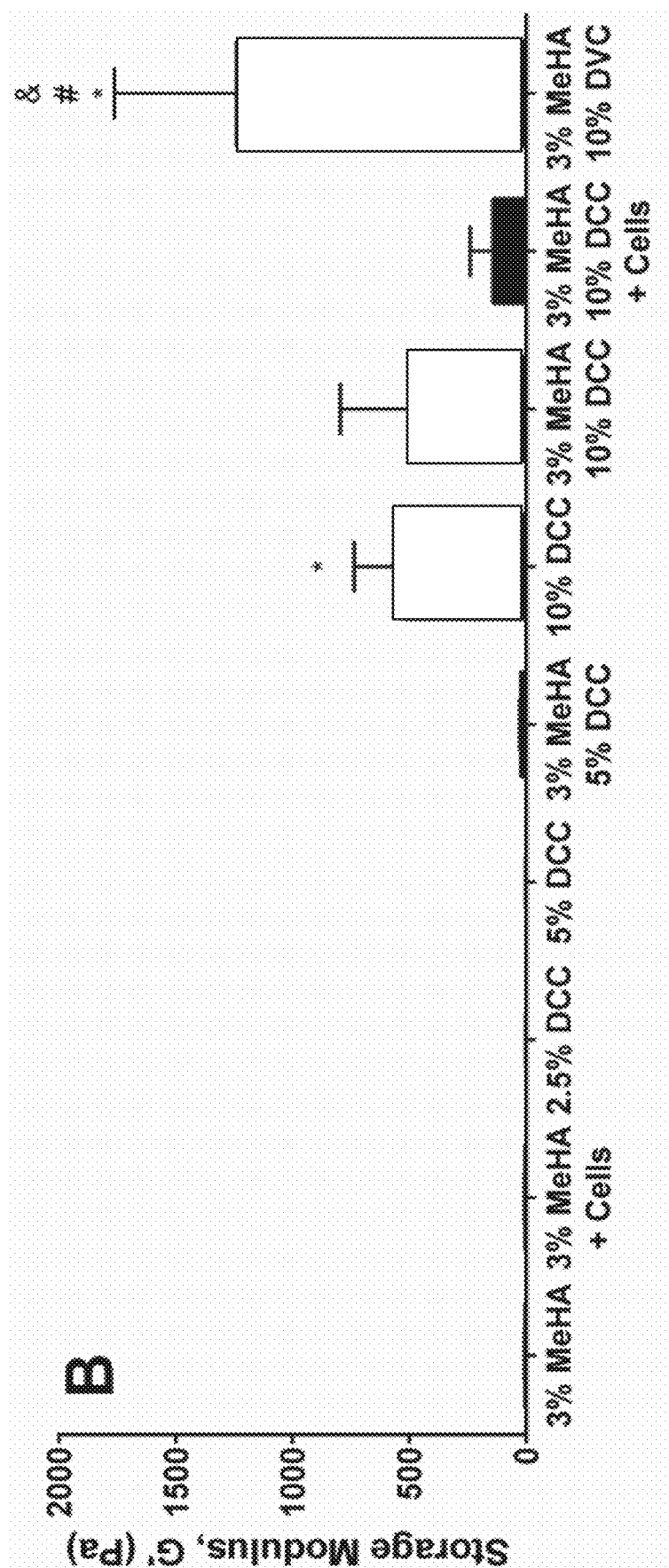
FIG. 4B includes a graph showing the comparative storage modulus for different hydrogel precursor compositions with DCC versus DVC.

All of the groups exhibited viscoelastic behavior, as indicated by a measurable storage modulus. However, the storage modulus of the MeHA+DVC group was significantly higher than all of the other groups at 1240±520 Pa, which was 58, 2.4, 2.6, and 8.8 times higher than the MeHA+5% DCC, 10% DCC, MeHA+10% DCC, and the cellular MeHA+10% DCC cellular groups, respectively, which were the groups that had a storage modulus greater than 20 Pa (FIG. 4B).

Throughout the entire culture period, the MeHA+5% DCC and MeHA+10% DCC groups never expressed collagen II. At 1 day, the rest of the groups did not have any significant differences. At 1 week, the MeHA+TGF-β$_3$ group did not express collagen II, and there were no significant differences in expression between the remaining groups. At 2 weeks, the only groups expressing collagen II were the MeHA+10% DCC+TGF-β$_3$ and the MeHA+DVC groups, although the difference between them was not significant. At 3 weeks and 6 weeks, the only group expressing collagen II was the MeHA+DVC group, which had a relative collagen II expression that was 180 and 320 times larger than the calibrator group (i.e., MeHA group at day 1), respectively (FIG. 5A). As such, the use of DVC particles can increase collagen II expression over time, which can be beneficial for chondrogenesis.

Figure 5B:
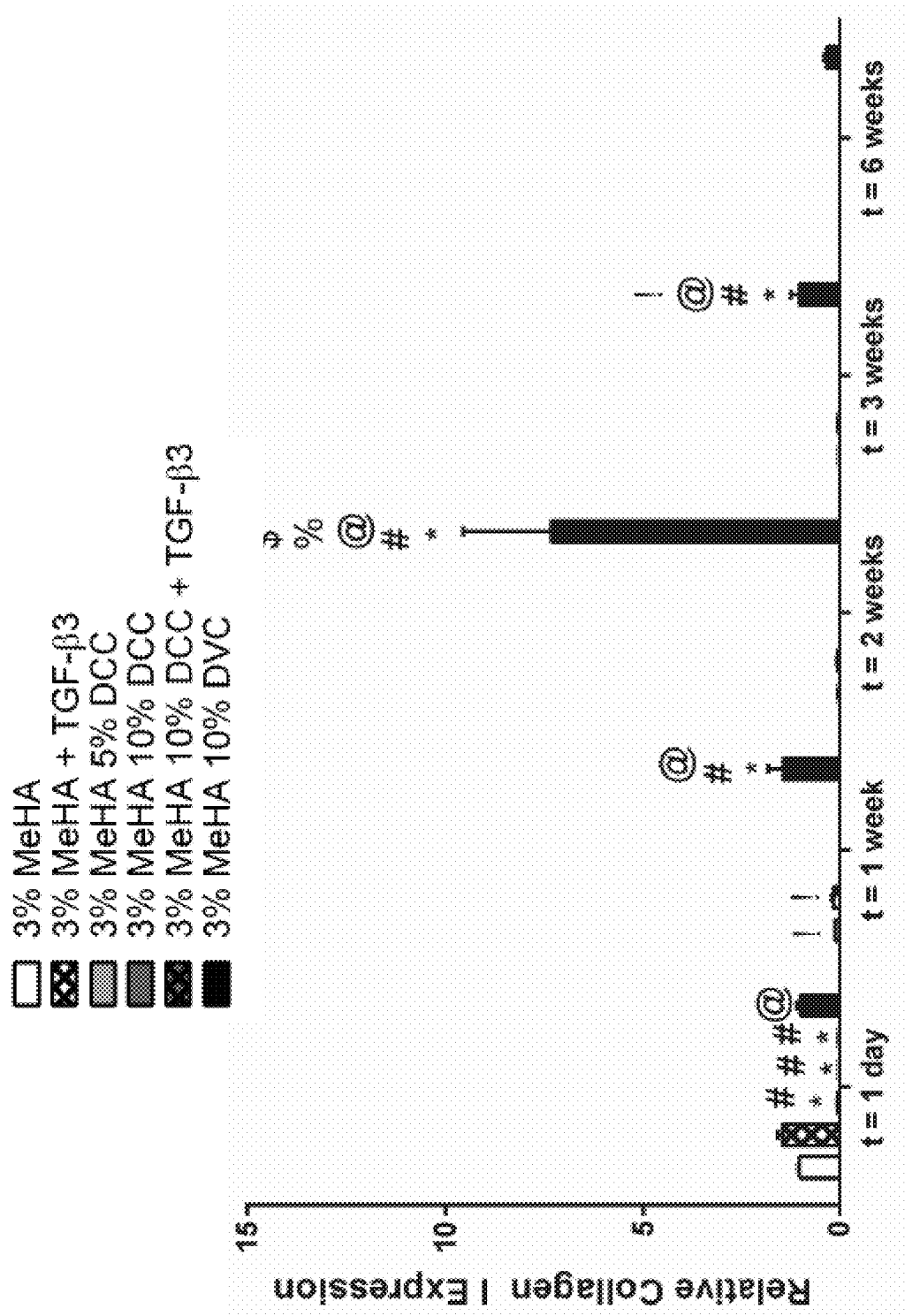
FIG. 5B includes a graph showing the comparative relative collagen I expression for different hydrogel precursor compositions with DCC versus DVC.

At 1 day, the DCC containing groups had at least 98% less collagen I expression than the MeHA group (FIG. 5B). By 2 weeks, the relative collagen I expression of MeHA+DVC increased to 304 times the MeHA group value. However, that expression significantly decreased by 86% at 3 weeks, but was still 99 times larger than the relative expression of the MeHA group. Although the collagen I expression reduced significantly from 1 day to 1 week for both the cellular and acellular MeHA groups, the collagen I expression for these and all groups but the MeHA+DVC groups remained steady the rest of the 6 weeks.

Figure 5C:
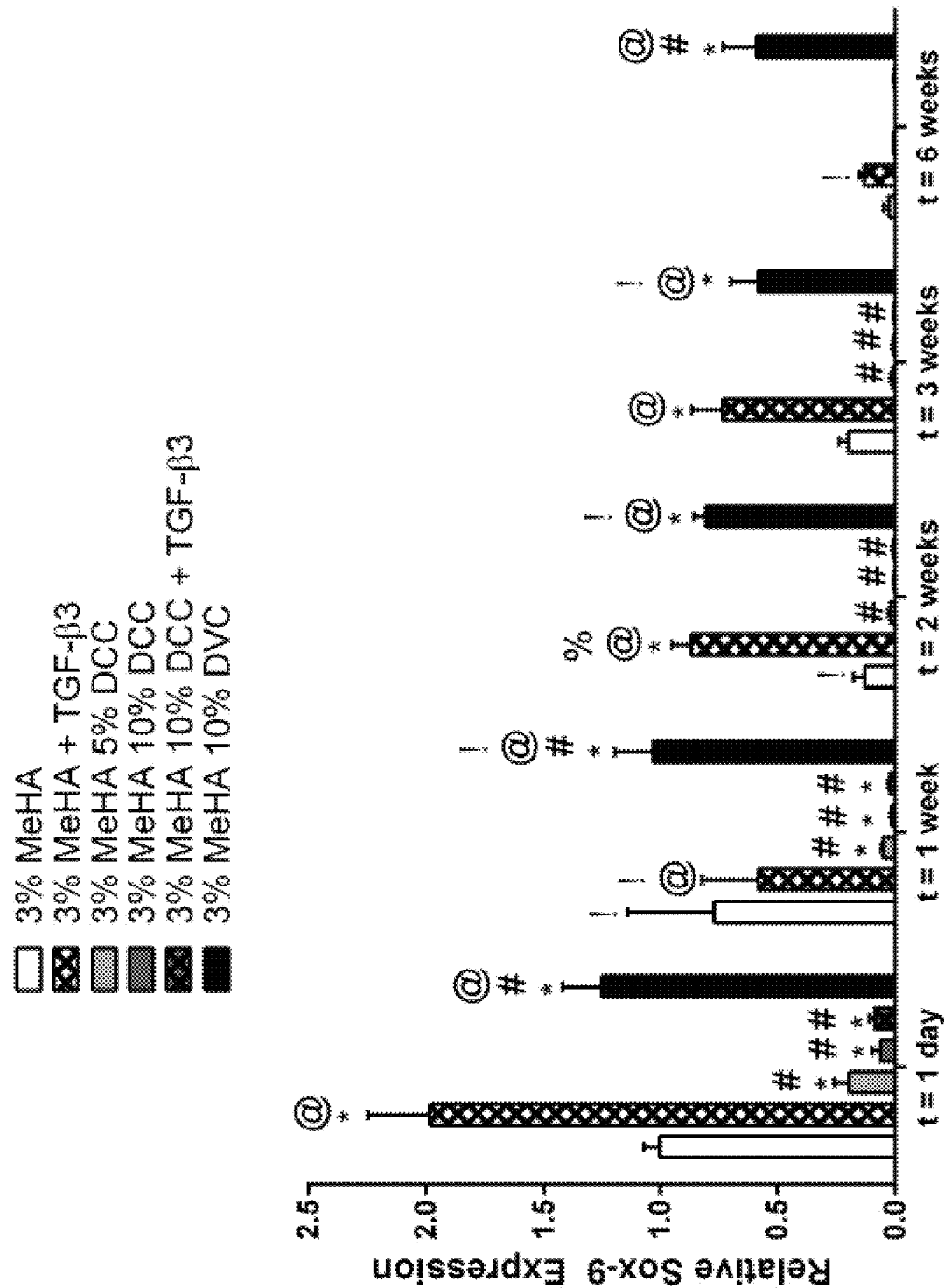
FIG. 5C includes a graph showing the comparative relative Sox-9 expression for different hydrogel precursor compositions with DCC versus DVC.

The MeHA+TGF-β$_3$ and MeHA+DVC groups had significantly higher Sox-9 expression than the groups containing DCC from 1 day to 3 weeks, where the relative expression was 2 and 1.3 times the MeHA group, respectively at day 1, and was 3.7 and 3 times larger than the MeHA group at 3 weeks (FIG. 5C). At 6 weeks, the DVC group had significantly higher Sox-9 expression than all other groups, where its expression was 4.4 and 109 times higher than the MeHA+TGF-β$_3$ and the MeHA+10% DCC+TGF-β$_3$ groups, respectively.

Figure 5D:
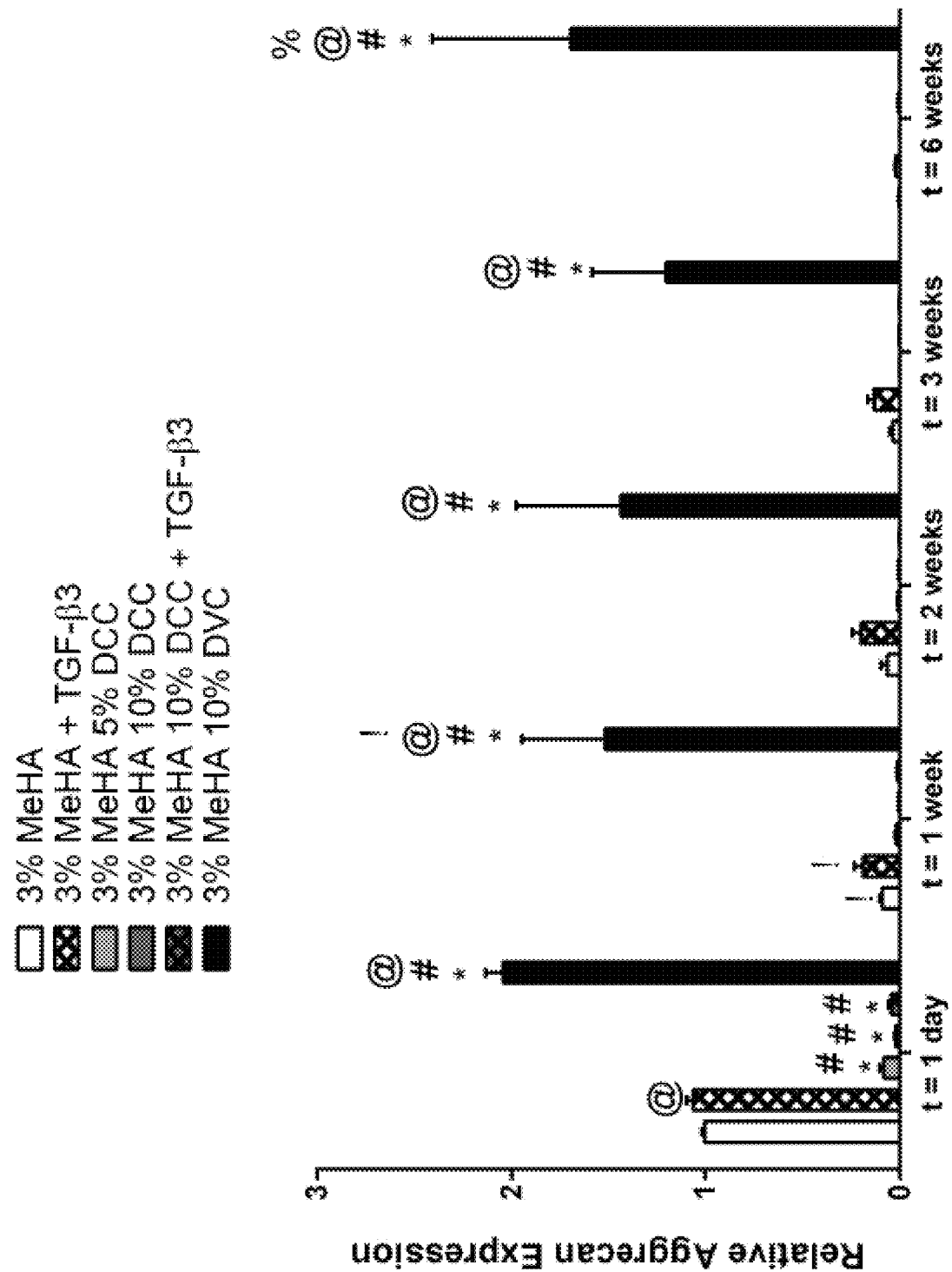
FIG. 5D includes a graph showing the comparative relative aggrecan expression for different hydrogel precursor compositions with DCC versus DVC.

At day 1, the relative aggrecan expression of the DCC containing groups was significantly lower than the MeHA group, whereas the relative expression of MeHA+DVC group was 2 times higher than the MeHA group (FIG. 5D). Over the culture period, both the cellular and acellular MeHA groups significantly reduced their aggrecan expression, however the MeHA+DVC group remained significantly higher than MeHA and all DCC groups over the 6 weeks. Additionally, the MeHA+DVC group's relative aggrecan expression was 2, 17, 22, 34, and 410 times higher than that of MeHA at 1 day, 1 week, 2 weeks, 3 weeks, and 6 weeks, respectively. Lastly, the relative aggrecan expression of the MeHA+DVC group at 6 weeks was 80 and 585 times higher than that of the MeHA+TGF-$\beta_3$ and the MeHA+10% DCC+TGF-$\beta_3$ groups, respectively.

The data shows that the DVC particles had improvements in expression of Collagen II, Sox-9 and aggrecan. Also, DVC particles did not increase Collagen I after 6 weeks. In addition to DVC having superior rheological properties, the DVC invoked superior chondroinductivity in comparison to DCC microparticles. For collagen II, Sox-9, and aggrecan expression, the MeHA+DVC group repeatedly outperformed the DCC containing groups, even when the DCC groups were exposed to TGF-$\beta_3$. The inclusion of DVC resulted in the gels retaining their original volumes throughout culture. Interestingly, encapsulation of DVC and cells together significantly increased the compressive modulus compared to the acellular MeHA+DVC control and all MeHA+DCC groups, which suggests that there may be superior cell-matrix interaction by incorporating DVC rather than DCC with cells, and gives further reasoning to support the use of DVC over DCC. Thus, DVC particles can provide improvements over DCC particles in colloidal gels as prehydrogels and in the hydrogels.

The yield stress (e.g., improved with DVC particles) denotes the threshold where a solution transitions between an elastic solid and a pseudoplastic liquid, and exhibiting a yield stress is crucial because it will prevent the hydrogel precursor from flowing away, keeping the material at the site of interest until crosslinking. In a surgical context, a material that exhibits a yield stress would allow a surgeon to appropriately shape and contour the material to the defect site before crosslinking it in place.

In one embodiment, an implantable composition can include methacrylated solubilized devitalized cartilage (MeSDVC). In one aspect, the implantable composition can include devitalized cartilage (DVC) particles in the MeSDVC. In one aspect, the implantable composition can include water, wherein the MeSDVC is crosslinked in the form of a hydrogel. In one aspect, the implantable composition can include water, wherein the MeSDVC is crosslinked around the DVC particles in the form of a hydrogel. In one aspect, the implantable composition can include a bioactive agent contained in the MeSDVC with or without the DVC. In one aspect, the MeSDVC is present from about 2.5% (w/v) to about 30% (w/v). In one aspect, the MeSDVC is present from about 2.5% (w/v) to about 30% (w/v); and the DVC particles are present from about 2.5% (w/v) to about 30% (w/v). In one aspect, the implantable composition can include the MeSDVC being uncrosslinked with a yield stress of from about 200 Pa to about 1000 Pa. In one aspect, the implantable composition can include the MeSDVC is uncrosslinked but has DVC particles and has a yield stress of from about 1000 Pa to about 2000 Pa.

In one embodiment, a method of preparing solubilized devitalized cartilage (SDVC) can include: providing DVC particles; mixing the DVC particles with acid to make an acidic DVC composition; adding pepsin to the acidic DVC composition to form a digested composition; and adding a base to the digested composition to neutralize the pH to physiological pH so as to form the SDVC. In one aspect, the method can include stirring the digested composition to allow the pepsin to digest components in the DVC composition. In one aspect, the method can include removing any unsolubilized DVC from the SDVC.

In one embodiment, a method of preparing methacrylated solubilized devitalized cartilage (MeSDVC), can include: providing the solubilized devitalized cartilage (SDVC) of one of the embodiments; dissolving the SDVC in water; adding an organic solvent to make a water:solvent solution; adding glycidyl methacrylate to the water:solvent solution; and stirring until obtaining methacrylated solubilized devitalized cartilage (MeSDVC) in the water:solvent solution. In one aspect, the organic solvent is acetone. In one aspect, the method further includes adding trimethylamine and tetrabutyl ammonium bromide along with the glycidyl methacrylate.

In one embodiment, a method of forming a hydrogel implant can include: providing a crosslinkable composition having methacrylated solubilized devitalized cartilage (MeSDVC), wherein the crosslinkable composition has a yield stress; implanting the crosslinkable composition; and crosslinking the crosslinkable composition so as to form a hydrogel therefrom. In one aspect, the crosslinkable composition having the yield stress further comprises devitalized cartilage (DVC) particles. In one aspect, the method can include: placing the crosslinkable composition into a defect in a tissue; shaping the crosslinkable composition in the defect; and crosslinking the crosslinkable composition in the defect to form the hydrogel. In one aspect, the tissue having the defect is cartilage.

It has also been found that colloidal gels can exhibit a yield stress by incorporating hyaluronic acid nanoparticles into methacrylated hyaluronic acid (MeHA) gels, and such nanoparticles and MeHA may be employed with the aspects of the technology described herein. However, the hyaluronic acid nanoparticles and/or MeHA gels may be specifically excluded from some embodiments of the colloidal gels and hydrogels formed therefrom.

In one embodiment, DCC can be used as a tissue scaffold material. DCC includes components that can be used as building blocks of cartilage, such as glycosaminoglycans (GAGs), and collagen, and may include bioactive proteins to promote attachment, growth, and differentiation of cells on a tissue scaffold material. The DCC can be formed into nanoparticles for inclusion in a colloidal gel that is cured or crosslinked into a hydrogel, and which may facilitate cellular attachments and influence chondrogenic gene expression. Accordingly, DCC matrix or particulates (e.g., nanoparticles) can be used as a hydrogel component in colloidal gels described herein as well as the hydrogels formed therefrom. However, DCC matrix or particulates (e.g., nanoparticles) may be specifically excluded from some embodiments of the colloidal gels and hydrogels formed therefrom.

Moreover, the DCC matrix or particles, MeDCC matrix or particles, or MeHA matrix may be used with the DVC and/or MeDVC matrix and/or particles for use as tissue scaffolds.

In one embodiment, a method can combine the colloidal gels (e.g., MeDVC or MeSDVC with DVC particles) with crosslinked hyaluronic acid hydrogels to form a hydrogel suitable for load-bearing applications that exhibits a yield stress prior to crosslinking The yield stress, the threshold level where a solution transitions from an elastic solid to a pseudoplastic liquid, allows a surgeon to mold and shape the material into the defect site without the concern that the material will flow or leak from the defect.

EXAMPLES

DVC Processing

Articular cartilage is obtained, washed, and frozen. Thawed cartilage is mixed with dry ice and coarsely ground using a cryogenic tissue grinder (BioSpec Products, Bartlesville, Okla.). The dry ice was allowed to evaporate overnight in the freezer, where the cartilage was then referred to as devitalized cartilage (DVC), and then the DVC was lyophilized. The DVC was then cryoground into a fine powder using a freezer-mill (SPEX SamplePrep, Metuchen, N.J.) and was lyophilized again overnight. The DVC powder was then filtered using a 106 μm mesh (ThermoFisher Scientific, Waltham, Mass.) to remove large particles and then frozen until use.

Preparing SDVC

The DVC powder was solubilized. First, DVC powder was mixed in 0.1 M HCl at a concentration of 10 mg DVC per 1 mL HCl. Pepsin was then added to the solution at a concentration of 1 mg/mL. The mixture was then stirred at room temperature. The solution was then brought to physiological pH by adding 1 M NaOH. This solubilized DVC powder (SDVC) was then centrifuged at 10,000×g for 3 min to pellet any unsolubilized particulates, and the supernatant was frozen and lyophilized and later used to make methacrylated SDVC (MeSDVC).

Preparing MeSDVC

The MeSDVC was created by reacting SDVC with 20 fold molar excess glycidyl methacrylate (Sigma-Aldrich, St. Louis, Mo.) in the presence of trimethylamine and tetrabutyl ammonium bromide (Sigma-Aldrich) in a 1:3 acetone:water mixture at a concentration of 1 g SDVC for every 150 mL solution. This solution was then stirred. The molar excess was approximated based on reacting one glycidyl methacrylate group to every monomer present in the solution and with the assumption that all monomers were hyaluronic acid. After 6 days, the MeSDVC was then precipitated in excess acetone, was dialyzed for 2 days in DI water, and then was lyophilized Successful methacrylation was confirmed using 1H NMR (Avance AV-III 500, Bruker).

Preparation of Precursor Hydrogel Pastes

Precursor hydrogel pastes were created by first measuring the desired weight percent of MeSDVC and DVC in a mini-centrifuge tube. All materials used for future cell encapsulation were then sterilized with ethylene oxide prior to use and were handled under sterile conditions thereafter. Water was added to form the pastes. The pastes were mixed with a photoinitiator solution.

Rheological Testing of Hydrogel Precursors

Prior to crosslinking the hydrogel precursor pastes, the precursor solutions were shaped into spheres to demonstrate their shaping capabilities, and they were then loaded into a 3 mL syringe and extruded onto a glass slide to macroscopically observe shape retention. The gels were extruded in a wavy line appearance to observe whether the formulations could maintain shaping after crosslinking.

Preparation of Hydrogels

The precursor hydrogel pastes were prepared and then subjected to light curing so as to crosslink the MeSDVC around the DVC particles. The other hydrogels were prepared with similar routines or as known in the art.

Mechanical Testing of Crosslinked Hydrogels

After swelling to equilibrium for 24 hours in either complete or incomplete chondrogenic medium, mechanical testing was performed as known in the art.

Swelling Degree and Volume

Gels that were swollen to equilibrium were weighed 1 day after crosslinking and were then frozen and lyophilized (n=5). The dry weight was then recorded and the swelling degree was calculated as the ratio of total wet mass to dry mass. From the diameter and height readings recorded during mechanical testing, the volume of each gel (n=5) was calculated at 1 day and after 6 weeks of culture.

Biochemical Content, Gene Expression, and Histological Analysis

The biochemical content, gene expression, and histological analysis were performed as known in the art.

The incorporated provisional provides methodologies to supplement the experimental methods described herein.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein and especially in the appended claims (e.g., bodies of the appended claims), are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at" least one and one or more to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc."

is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

The invention claimed is:

1. An implantable colloidal gel composition comprising:
methacrylated solubilized devitalized cartilage (MeSDVC) matrix, wherein the MeSDVC matrix is not crosslinked or decellularized; and
devitalized cartilage (DVC) particles in the MeSDVC matrix, wherein the DVC particles are not methacrylated or decellularized or crosslinked with the MeSDVC matrix,
wherein the MeSDVC matrix is devoid of decellularized cartilage (DCC) particles.

2. The composition of claim 1, further comprising water, wherein the MeSDVC matrix and DVC particles form paste with the water, wherein the paste is not crosslinked and is non-Newtonian, wherein the paste has a yield stress.

3. An implantable crosslinked hydrogel composition comprising:
a crosslinked methacrylated solubilized devitalized cartilage (MeSDVC) matrix that is not decellularized;
devitalized cartilage (DVC) particles in the MeSDVC matrix, wherein the DVC particles are not methacrylated or decellularized or crosslinked with the MeSDVC matrix; and
water,
wherein the MeSDVC matrix is crosslinked around the DVC particles in the form of the hydrogel,
wherein the MeSDVC matrix is devoid of decellularized cartilage (DCC) particles.

4. The composition of claim 1, further comprising a bioactive agent contained in the MeSDVC matrix, wherein the bioactive agent is selected from cartilage growth factors, bone growth factors, or tissue growth factors other than for cartilage or bone, and drugs.

5. The composition of claim 3, further comprising a bioactive agent contained in the MeSDVC matrix, wherein the bioactive agent is selected from a drug, cartilage growth factors, bone growth factors, or tissue growth factors other than for cartilage or bone.

6. The composition of claim 2, wherein:
the MeSDVC matrix is present from about 2.5% (w/v) to about 30% (w/v); and
the DVC particles are present from about 2.5% (w/v) to about 30% (w/v).

7. The composition of claim 3, wherein:
the MeSDVC matrix is present from about 2.5% (w/v) to about 30% (w/v); and
the DVC particles are present from about 2.5% (w/v) to about 30% (w/v).

8. The composition of claim 1, wherein the MeSDVC matrix is uncrosslinked and the composition has a yield stress of from about 1000 Pa to about 2000 Pa.

9. A method of forming a hydrogel implant, the method comprising:
providing the paste composition of claim 2 having the MeSDVC and DVC particles with a crosslinking activator, wherein the crosslinkable composition has a yield stress;
implanting the paste composition into a subject; and
crosslinking the paste composition so as to form a hydrogel therefrom in the subject.

10. The method of claim 9, comprising:
placing the paste composition into a defect in a tissue;
shaping the paste composition in the defect; and
crosslinking the paste composition in the defect to form the hydrogel.

11. The method of claim 10, wherein the tissue is cartilage.

12. The composition of claim 1, wherein the DVC particles are larger than 10 microns.

13. The composition of claim 1, wherein the DVC particles are smaller than 200 microns.

14. The composition of claim 2, further comprising living cells in the paste composition.

15. The composition of claim 3, further comprising living cells in the crosslinked hydrogel.

16. The composition of claim 1, wherein:
the MeSDVC matrix is present from about 10% (w/v); and
the DVC particles are present from about 10% (w/v).

17. The composition of claim 3, wherein the DVC particles are less than 300 microns.

18. The composition of claim 3, wherein the DVC particles are smaller than 100 nm.

19. The composition of claim 3, wherein the DVC particles are smaller than 50 nm.

20. The composition of claim 2, wherein the composition is shape stable with a yield stress.

* * * * *